United States Patent
Yang

(10) Patent No.: US 7,628,158 B2
(45) Date of Patent: Dec. 8, 2009

(54) CUPPING MOXA UTENSIL AS HERB MEDICAL AUXILIARY

(75) Inventor: Hanjo Yang, Busan (KR)

(73) Assignee: Hanji Co., Ltd., Busan (KR)

( * ) Notice: Subject to any disclaimer, the term of this patent is extended or adjusted under 35 U.S.C. 154(b) by 449 days.

(21) Appl. No.: 10/547,965

(22) PCT Filed: Oct. 20, 2003

(86) PCT No.: PCT/KR03/02197

§ 371 (c)(1),
(2), (4) Date: Sep. 8, 2005

(87) PCT Pub. No.: WO2005/007062

PCT Pub. Date: Jan. 27, 2005

(65) Prior Publication Data

US 2006/0180160 A1    Aug. 17, 2006

(30) Foreign Application Priority Data

Jul. 23, 2003  (KR) .................. 20-2003-0023807 U
Aug. 7, 2003   (KR) ...................... 10-2003-0054550

(51) Int. Cl.
*A61B 19/00* (2006.01)
(52) U.S. Cl. ...................................... 128/897
(58) Field of Classification Search ................ 128/897; 600/9; 604/23–24
See application file for complete search history.

(56) References Cited

U.S. PATENT DOCUMENTS

| 3,946,733 | A | * | 3/1976 | Han | 604/24 |
| 4,203,438 | A | * | 5/1980 | Shiu | 604/24 |
| 5,904,664 | A | * | 5/1999 | Kim | 604/19 |

* cited by examiner

*Primary Examiner*—Charles A Marmor, II
*Assistant Examiner*—Christine D Hopkins
(74) *Attorney, Agent, or Firm*—John K. Park; Park Law Firm

(57) ABSTRACT

The present invention relates generally to a cupping and moxibustion device for assisting traditional East-Asian medicine. In more detail, an inner wall is provided in the lower portion of a body so that the lower portion is divided into a moxibustion part located in the inner part of the lower portion and a cupping part located in the outer part of the lower portion, a moxa pot is held above the moxibustion part, thus carrying out moxibustion, and an air discharge hole is formed on the outer wall of the body, an opening and closing unit is fitted into the air discharge hole, and air is discharged from the cupping part to the outside of the device to depressurize the cupping part, thus carrying out cupping.

In this case, an air suction hole is formed on a lid provided on the upper end of the body, an air pump is connected to the air suction hole, and air is supplied to allow moxa contained in the moxa pot to be smoothly combusted. Furthermore, a smoke discharge hole is formed on the side of the body and, thus, smoke generated at the time of combusting the moxa is discharged to the outside of the body.

2 Claims, 3 Drawing Sheets

CUPPING MOXA UTENSIL AS HERB MEDICAL AUXILIARY

TECHNICAL FIELD

The present invention relates generally to a cupping and moxibustion device, and more particularly to a cupping and moxibustion device for assisting traditional East-Asian medicine, whose lower portion is composed of two concentric parts, so that moxibustion is carried out in the inner part of the lower portion and cupping is carried out in the outer part of the lower portion.

BACKGROUND ART

In general, moxa is a perennial grass belonging to the chrysanthemum family. Moxa has strong alkalinity, has been widely used for culinary and medicinal purposes by folks, and contains abundant chlorophyll, vegetable fibers, mineral of good quality and various vitamins.

In traditional East-Asian medicine, acupuncture and moxibustion has been used as methods of improve immunity and vitality by removing stagnated blood due to abnormalities in the circulation of blood and Qi and warming Qi. Since the performance of acupuncture requires the assistance of specialists, moxibustion has been widely utilized by folks from old times.

Existing general moxibustion is classified into direct moxibustion of carrying out moxibustion with moxa placed on the skin of a patient and indirect moxibustion of carrying out moxibustion with moxa placed on garlic, ginger or salt. These types of moxibustion are all problematic in that they generate heat and the influences (smoke and vapor) of moxa are dispersed over an open indoor space to cause inconvenience and it is difficult to use the moxibustion due to difficulty in controlling temperature.

The cupping for promoting the immunity and vitality of humans by eliminating stagnated blood due to abnormality in the flow of Qi and blood and warming Qi so that Qi and blood are smoothly circulated has been also utilized widely in traditional East-Asian medicine and folk therapy. The shapes and kinds of cupping pots are various, and are mostly made of material, such as an animal horn, glass, plastic, wood and ceramic. The cupping may be classified into a single pot method of attaching a single cupping pot to the skin of a patient, a multiple pot method of attaching a plurality of cupping pots to the skin of a patient, an intermittent pot method of repeating the attaching and detaching of cupping pots to and from the skin of a patent, and a moving pot method of reciprocating cupping pots on the skin of the patient while being at the state of attaching cupping pots to the skin after applying lubricating oil to the skin. The cupping may also be classified into dry cupping of causing engorgement by attaching cupping pots to the skin of a patient, wet cupping of discharging blood by attaching cupping pots after applying acupuncture, and foaming cupping of causing skin foaming by attaching cupping pots to the skin of the patient under a high pressure.

In conventional cupping, since the effect of treatment can be achieved only by maintaining 10 to 40 cupping pots on the skin of a patient for a long time, the treatment requires a long time, and cupping pots are attached on a region without stagnated blood and, thus, causes a side effect because a plurality of cupping pots are employed. Furthermore, since the performance of cupping functions only to raise stagnated blood to the hypodermis of the skin, the effect of the treatment is weak. Accordingly, the conventional cupping is problematic in that the cupping has to be performed many times.

DISCLOSURE OF THE INVENTION

Accordingly, the present invention has been made keeping in mind the above problems occurring in the prior art, and an object of the present invention is to provide a cupping and moxibustion device that is capable of simultaneously carrying out moxibustion in the inner part thereof and cupping in the outer part thereof. Another object of the present invention is to provide a cupping and moxibustion device that is capable of discharging smoke generated at the time of moxibustion to the outside and facilitating the control of the temperature of the moxibustion.

In order to accomplish the above object, an inner wall is provided in the lower portion of a body so that the lower portion is divided into a moxibustion part located in the inner part of the lower portion and a cupping part located in the outer part of the lower portion, a moxa pot is held above the moxibustion part, thus carrying out moxibustion, and an air discharge hole is formed on the outer wall of the body, an opening and closing unit is fitted into the air discharge hole, and air is discharged from the cupping part to the outside of the device to depressurize the cupping part, thus carrying out cupping.

In this case, an air suction hole is formed on a lid provided on the upper end of the body, an air pump is connected to the air suction hole, and air is supplied to desirably combust moxa contained in the moxa pot. Furthermore, a smoke discharge hole is formed on the side of the body and, thus, smoke generated at the time of combusting the moxa is discharged to the outside of the body.

The air pump is connected to the body having the smoke discharge hole specially designed and connected to the lid having the air suction hole. The air pump forcibly induces air into the body when it is operated, so that the moxa contained inside of the moxa pot is burned. At this time, heat and smoke of the moxa are moved toward the lower portion of the moxibustion part, and then, discharged to the outside through the smoke discharge hole. By the above structure, the present invention provides an effective moxibustion to the patient since the heat and smoke of the moxa effectively act on the skin of the patient. Furthermore, the seat located on the upper portion of the body to catch the moxa pot therein, and moxibustion part and the cupping part respectively located on the lower portion of the body are formed integrally in such a way as to form the body, and the moxibustion part and the cupping part are divided by the inner wall.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
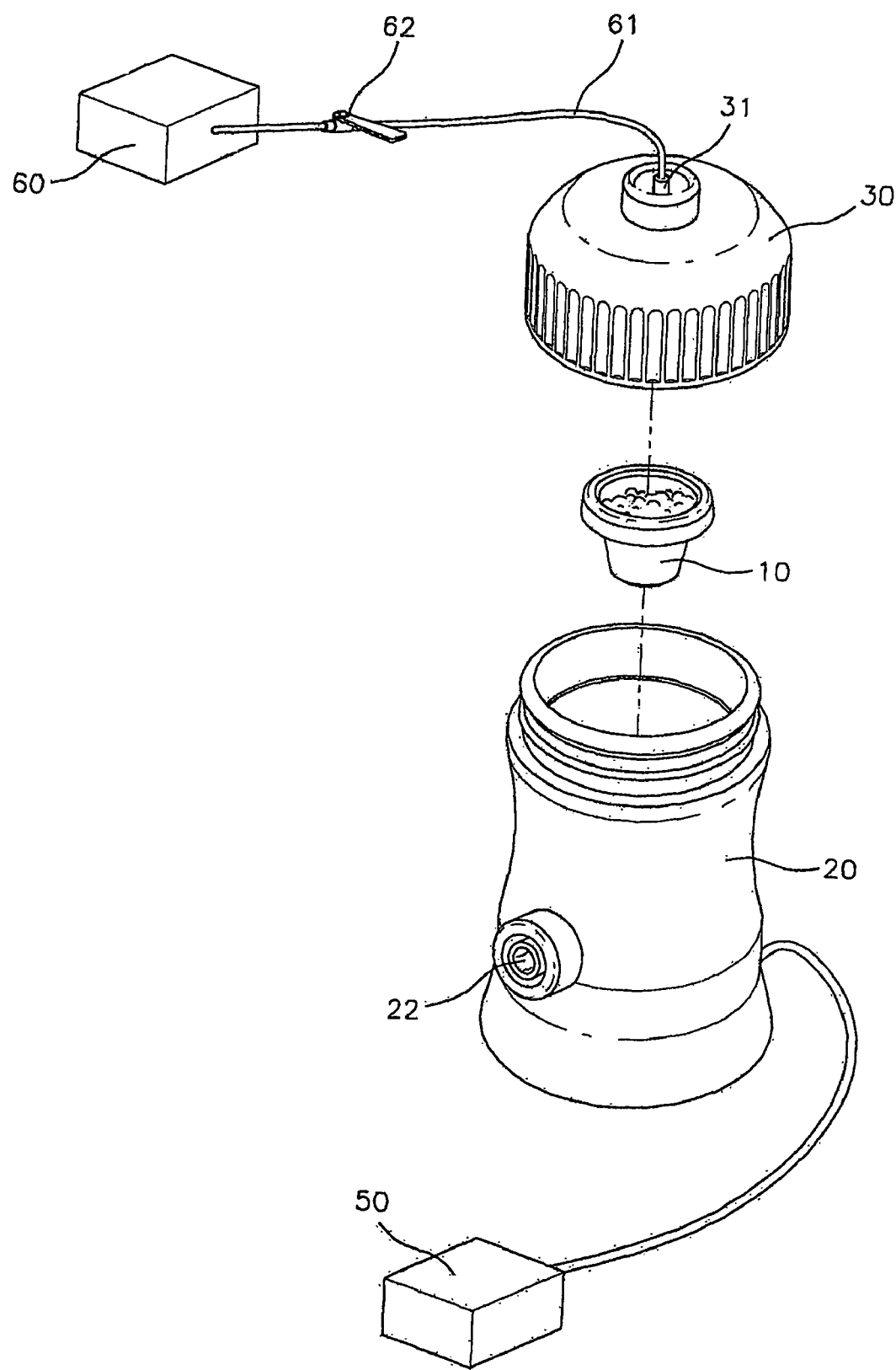
FIG. 1 is an exploded perspective view of a cupping and moxibustion device for assisting traditional East-Asian medicine.
Figure 2:
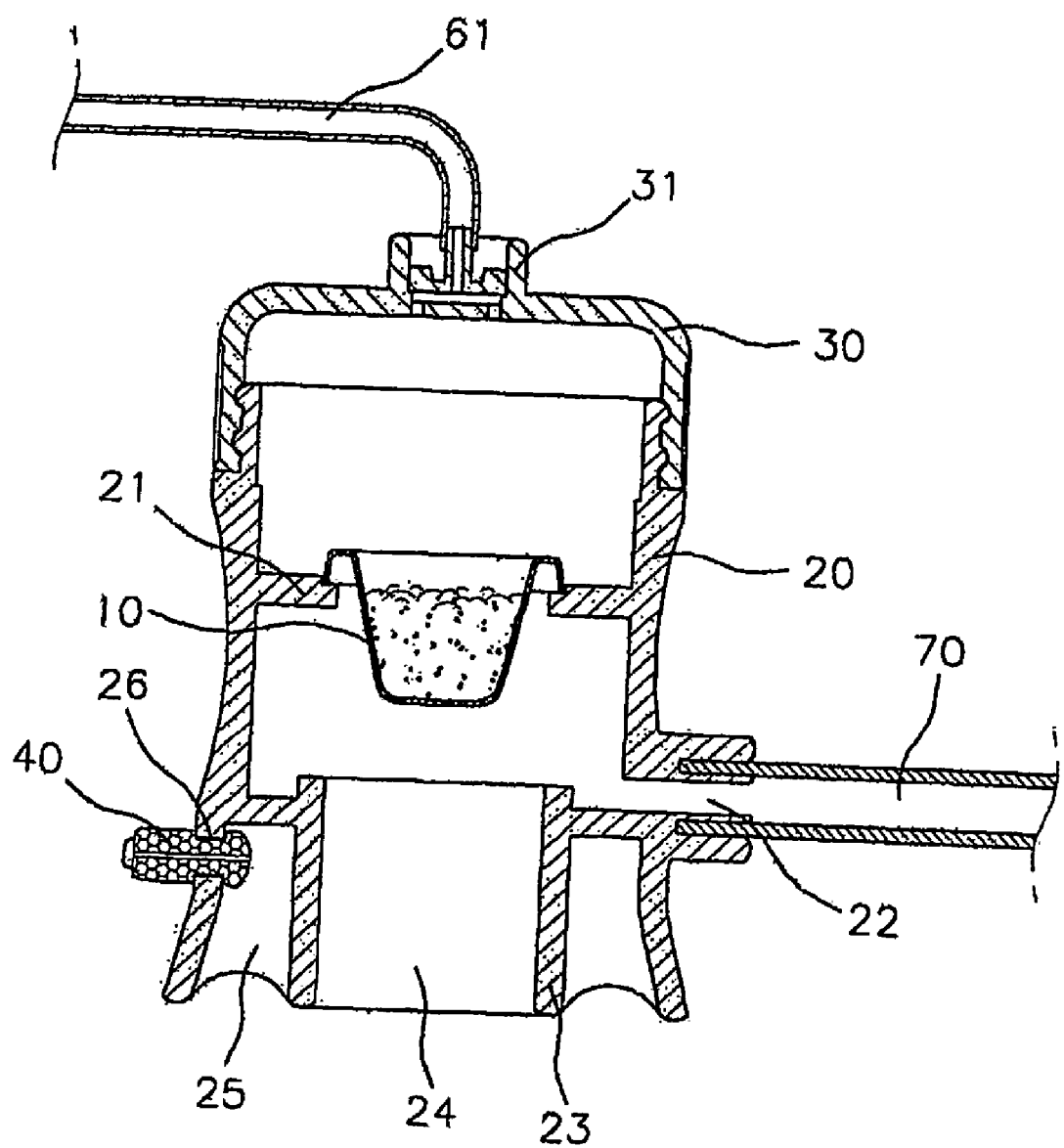
FIG. 2 is a partial cross-section of the cupping and moxibustion device for assisting traditional East-Asian medicine.
Figure 3:
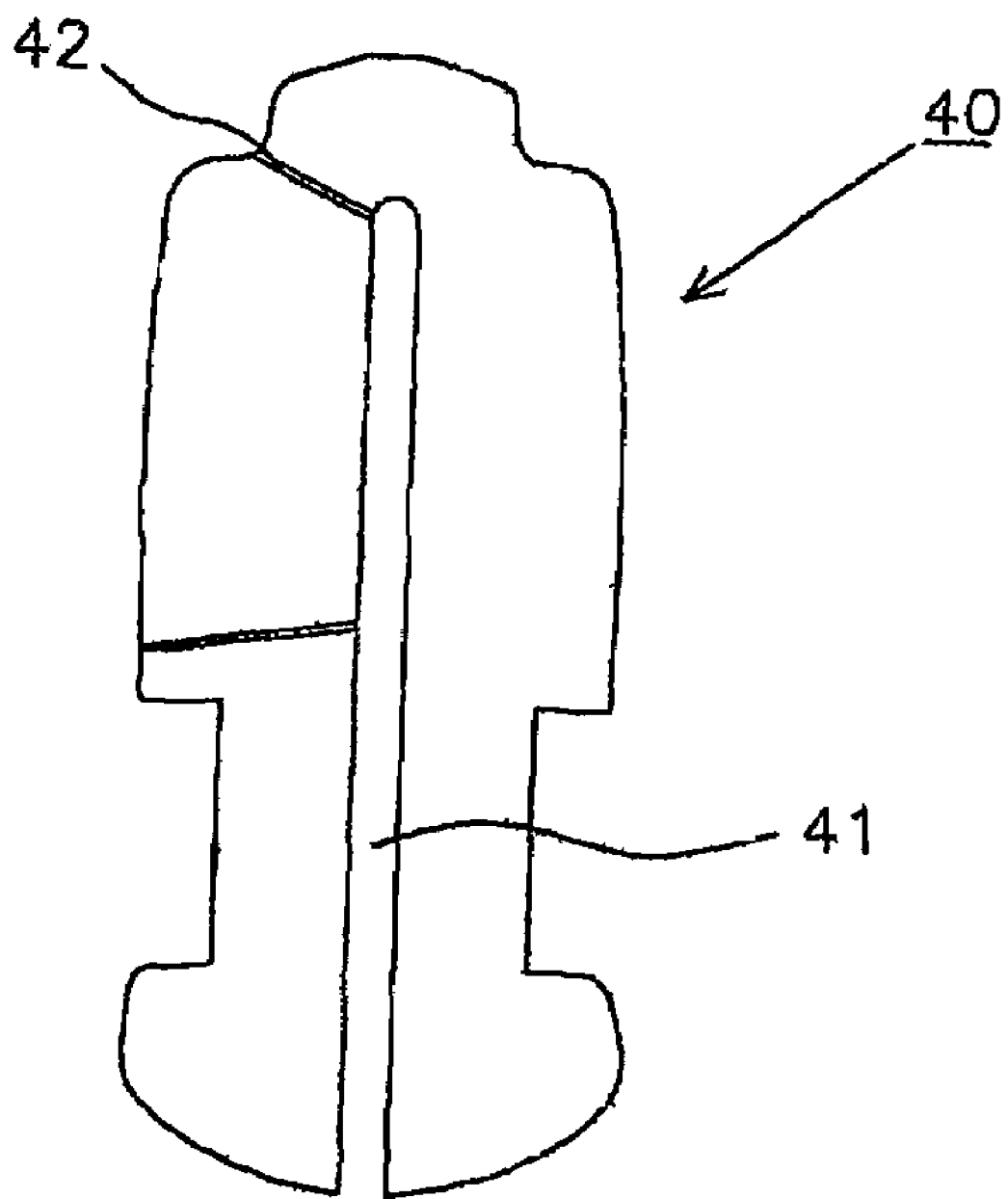
FIG. 3 is a cross-section of an opening and closing unit.

A cupping and moxibustion device for assisting traditional East-Asian medicine according to an embodiment of the present invention will be described in detail with reference to the attached drawings below.

The cupping and moxibustion device for assisting traditional East-Asian medicine according to an embodiment of the present invention is largely comprised of a moxa holder 10, a body 20, a lid 30 and an opening and closing unit 40.

First, the moxa pot 10 is described below. The moxa pot 10 is closed at the top thereof and is provided with a plurality of through holes. Moxa is contained inside of the moxa pot 10. To be resistant to heat because moxa catches fire when used, and prevent heat from being transmitted to the body 20, the moxa pot 10 is manufactured by coating the outside of a moxa pot body made of aluminum with ceramic having a low heat-conductivity. The upper portion of the moxa pot 10 is bent outward so that it is caught on a seat 21 formed on the inside surface of the body 20 (the seat 21 will be described later).

The upper portion of the moxa pot 10 may have a diameter larger than that of the lower portion of the moxa pot 10 instead of being bent outward so that it can be caught by the seat 21.

Next, the body 20 is described. The body 20 may be classified into a moxa holding part, a moxibustion part 24, and a cupping part 25. The moxa holding part formed on the upper portion of the body 20 is opened at the upper end thereof, is threaded at the upper portion of the outside thereof, and is provided with the seat 21 projected from a part of the inside thereof, thus catching the moxa pot 10. A smoke discharge hole 22 is formed below the seat 21 to discharge the smoke of moxa. The smoke discharge hole 22 extends outward to be connected to a smoke discharge pipe 70. In this invention, one end of the smoke discharge pipe 70 is connected to the smoke discharge hole 22 and the other end of the smoke discharge pipe 70 is connected to the outside of a room so that smoke generated at the time of moxibustion is discharged to the outside of the room.

The lower portion of the body 20 may be divided into the moxibustion part 24 located in the inner part of the lower portion and the cupping part 25 located in the outer part of the lower portion. The moxibustion part 24 and the cupping part 25 are divided by an inner wall 23. The moxibustion part 24 is opened at the upper and lower ends thereof and, thus, forms a passage that transmits heat and smoke, generated when moxa held in the moxa holding part burns, to the skin of a patient. The cupping part 25 is divided from the moxa holding part and the moxibustion part 24 by the inner wall 23 and is provided with an outer wall formed by extending the outer wall of the moxa holding part downwardly. An air discharge hole 26 is formed on the outer wall of the cupping part 25 to eliminate air from the cupping part 25.

Next, the lid 30 is described below. The lid 30 is combined with the upper portion of the body 20 so that the smoke of moxa is prevented from being discharged from the body 20 to the outside of the device. The inside of the lid 20 is threaded so that the threaded portion of the lid 20 engages with the threaded portion of the body 20. In this case, a packing may be provided inside of the lid 30 to improve the sealing effect between the lid 30 and the body 20. Prominences and depressions may be formed on the outside of the lid 30 to facilitate the opening and closing of the lid 30.

An air suction hole 31 is formed on the top of the lid 30. The air suction hole 31 is extended upwardly to be connected to an end of an air suction pipe 61. The other end of the air suction pipe 61 is connected to an air pump 60 so that air can be drawn through the air suction hole. A valve 62 is mounted on the air suction pipe 61 to control the flow of air. The purpose of the valve 62 is to maintain the appropriate temperature of moxibustion by controlling the amount of air drawn into the inside of the body 20.

Next, the opening and closing unit 40 is described below. The opening and closing unit 40 is made of soft rubber or the like, and is inserted into the air discharge hole 26 of the body 20. A hole 41 is formed inside of the opening and closing unit 40 and communicates with the inside of the body 20. An incision 42 is formed through the projected portion of the opening and closing unit 40 so that the incision 42 is opened and the inside of the cupping part 25 communicates with the outside of the body 20 when the projected portion is pressurized from the outside of the device and the incision 42 is closed when the projected portion is depressurized.

Accordingly, when a compressor 50 is coupled to the opening and closing unit 40, the incision 42 is opened. When the compressor 50 is operated and, thus, air is discharged from the cupping part 25, the air pressure of the cupping part 25 is decreased. At this time, the compressor 50 is removed from the opening and closing unit 40, the incision 42 of the opening and closing unit 40 is closed and air is prevented from being drawn through the air discharge hole 26 from the outside of the device.

The operation of the moxibustion and cupping device for assisting traditional East-Asian medicine according to the embodiment of the present invention is described below.

After the lid 30 is removed from the body 20 and moxa is placed in the moxa pot 10, the moxa is ignited. The body 20 is closed to prevent smoke from leaking to the outside of the body 20 by putting the lid 30 on the body 20 after the moxa pot 10 is seated in the body 20. At this time, when the air suction pipe 61 connected to the air pump 60 is connected to the air suction hole 31 of the lid 30, and the smoke discharge pipe 70 is connected to the smoke discharge hole 22 at one end thereof and is extended to the outside of the room at the other end thereof.

After the cupping and moxibustion device is placed on the skin of the patient, the compressor 50 is connected to the air discharge hole 26, so that air is eliminated from the cupping part 25 and vacuum is formed in the cupping part 25. Air is drawn into the body 20 by operating the air pump 60 and opening the valve 62. Accordingly, the air moves from a position above the moxa pot 10 through the inside of the moxa pot 10 to the through holes formed on the bottom of the moxa pot 10. Further, the air moves downward together with the heat and smoke generated by the combustion of the moxa and, thus, applies moxibustion to the skin located below the moxibustion part 24. Thereafter, the smoke is discharged to the outside of the room through the smoke discharge hole 22 formed on the side of the body 20. In this case, the temperature of the moxibustion is maintained at a desired value by controlling the amount of air drawn into the body 20 using the valve 62 attached to the air suction pipe 61.

When the moxibustion is completed, the cupping and moxibustion device is removed from the skin, sap is removed by wiping out the skin.

INDUSTRIAL APPLICABILITY

As described above, in accordance with the cupping and moxibustion device for assisting traditional East-Asian medicine according to the present invention, stagnated blood is circulated by means of the moxibustion part located in the inner portion of the device under the action of the smoke and heat of moxibustion and the toxin of stagnated blood is discharged to the outside of the skin by means of the cupping part located in the outer portion of the device, thus maximizing the effect of treatment.

Furthermore, smoke can be discharged to the outside of a room, and the temperature of moxibustion can be automatically adjusted by controlling the amount of air drawn using the valve attached to the air suction pipe, thus facilitating the use of the device.

The invention claimed is:

1. A cupping and moxibustion device for assisting traditional East-Asian medicine, which includes a moxa pot located on the upper portion for containing moxa therein, a moxibustion part formed on the lower portion to communicate with the moxa pot, and a cupping part divided from the upper portion and the moxibustion part and located around the moxibustion part, comprising:
   a) a body having a seat formed therein for seating the moxa pot inside the body and a smoke discharge hole formed on a side thereof, the smoke discharge hole being located below the seat and above the moxibustion part to communicate with the moxa pot;
   b) a lid combined with the upper portion of the body and having an air suction hole communicating with the moxibustion part when it is combined with the body; and
   c) an air pump connected with the air suction hole to supply air into the body, whereby moxa contained in the moxa pot is burned when the air pump is operated and the air is forcibly induced into the body, at which time, heat and smoke of the moxa are moved downwardly toward the moxibustion part, and then, discharged to the outside through the smoke discharge hole,
   wherein the air pump is connected to the air suction hole and an air suction pipe, and a valve is mounted on the air suction pipe, whereby an amount of the air supplied into the body can be controlled,
   wherein the seat located on the upper portion of the body to catch the moxa pot therein, and moxibustion part and the cupping part respectively located on the lower portion are formed integrally in such a way as to form the body, and the moxibustion part and the cupping part are divided by the inner wall,
   wherein the moxibustion part comprises a lower end and the cupping part comprises a lower end, wherein the lower end of the moxibustion part and the lower end of the cupping part are aligned and disposed in a same plane, such that the cupping part keeps a cupped space enclosed by the cupping part and the lower end of the cupping part in a controllable low pressure.

2. The cupping and moxibustion device as set forth in claim 1, wherein the body includes an air discharge hole formed on the outer wall thereof to communicate with the cupping part, and an opening and closing unit is inserted into the air discharge hole, for maintaining pressure inside the cupped space by controlling an air flow between the inside and the outside of the cupping part independently from the moxibustion part.

* * * * *